(12) United States Patent
Buchanan et al.

(10) Patent No.: US 7,687,672 B2
(45) Date of Patent: Mar. 30, 2010

(54) IN-LINE PROCESS FOR GENERATING COMONOMER

(75) Inventors: John S. Buchanan, Lambertville, NJ (US); Timothy D. Shaffer, Hackettstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1076 days.

(21) Appl. No.: 11/346,651

(22) Filed: Feb. 3, 2006

(65) Prior Publication Data

US 2007/0185364 A1 Aug. 9, 2007

(51) Int. Cl.
*C07C 2/24* (2006.01)
(52) U.S. Cl. .................. 585/326; 585/324; 585/329; 585/512; 585/513; 585/514; 585/520; 585/527; 585/528; 585/530; 585/532
(58) Field of Classification Search ............... 585/523, 585/530, 512–514, 520, 527, 528, 532, 324, 585/326, 329
See application file for complete search history.

(56) References Cited

U.S. PATENT DOCUMENTS

| | | |
|---|---|---|
| 4,511,746 A | 4/1985 | Miller |
| 5,000,840 A | 3/1991 | Anthes et al. |
| 5,382,738 A | 1/1995 | Reagen et al. |
| 5,451,645 A | 9/1995 | Reagen et al. |
| 5,523,507 A | 6/1996 | Reagen et al. |
| 5,541,270 A | 7/1996 | Chinh et al. |
| 5,543,375 A | 8/1996 | Lashier et al. |
| 5,563,312 A | 10/1996 | Knudsen et al. |
| 5,859,303 A | 1/1999 | Lashier |
| 6,274,783 B1 | 8/2001 | Gildert et al. |

(Continued)

FOREIGN PATENT DOCUMENTS

EP 668 106 8/1995

(Continued)

OTHER PUBLICATIONS

J.T. Dixon et al., "Advances in Selective Ethylene Trimerisation—A Critical overview," Jrnl. of Organometallic Chemistry, vol. 689, 2004, pp. 3641-3668.

(Continued)

*Primary Examiner*—In Suk Bullock

(57) ABSTRACT

The present invention relates to an in-line method for generating comonomer, such as 1-hexene or 1-octene, from monomer, such as ethylene. The comonomer generated is directly transported, without isolation or storage, to a polyethylene polymerization reactor. The in-line method for generating comonomer includes the steps of providing an in-line comonomer synthesis reactor and a downstream gas/liquid phase separator prior to a polyethylene polymerization reactor; feeding ethylene monomer and a catalyst in a solvent to the comonomer synthesis reactor; reacting the ethylene monomer and the catalyst in solvent under reaction conditions to produce an effluent stream including ethylene monomer and comonomer; passing the effluent stream from the comonomer synthesis reactor to the downstream gas/liquid phase separator to separate a gas stream from a bottom stream, wherein the gas stream is a mixture of ethylene monomer, and comonomer; and passing the gas stream to the polyethylene polymerization reactor to provide the necessary comonomer input. The in-line method is useful in the production of LLDPE, and other branched polyethylene based polymers. Some benefits include process simplification and reduced capital and operating costs.

20 Claims, 3 Drawing Sheets

In-Line Process for Comonomer Generation

U.S. PATENT DOCUMENTS 6,423,791 B1 7/2002 Kral
6,800,702 B2 10/2004 Wass

FOREIGN PATENT DOCUMENTS

WO     WO 99/19280     4/1999
WO     WO 2004/056478     7/2004
WO     WO 2004/056479     7/2004

OTHER PUBLICATIONS

S. Naqvi, "1-Hexene From Ethylene by the Phillips Trimerization Technology," SRI Consulting PEP Review 95-1-8, http://www.sriconsulting.com/PEP/Reports/Phase_95/RW95-1-8/RW95-1-8.html.

In-Line Process for Comonomer Generation

Fixed Bed Reactors for In-Line Comonomer Generation with Catalyst in Tubes with Coolant Fixed Bed Reactors for In-Line Comonomer Generation with Cold Shot Cooling

IN-LINE PROCESS FOR GENERATING COMONOMER

FIELD OF THE INVENTION

The present invention relates to the field of reaction and separation processes. It more particularly relates to an improved method for generating comonomer from monomer. Still more particularly, the present invention relates to improved in-line process for generating 1-hexene and 1-octene from ethylene monomer for subsequent polyethylene polymerization.

BACKGROUND

Olefin polymerization, especially ethylene polymerization, can benefit from the addition of longer-chain comonomers, such as 1-hexene, and 1-octene, to produce linear low density polyethylene (LLDPE). LLDPE produced from 1-hexene and 1-octene accounts for a large percentage of the polyethylene resin market. In general, polyethylene plants buy hexene and octene, which are produced in separate plants that typically produce a range of even-numbered alpha olefins from ethylene. It can be expensive to purchase these materials, and they add to the complexity of storage and handling. An attractive alternative is to make the comonomer directly from the ethylene, if this can be done cleanly and economically. It would be perhaps most economical to do this in-situ in the polymerization reactor by altering the catalyst, however this is very difficult.

The review article "Advances in selective ethylene trimerisation—a critical review" by Dixon et al. (J. Organometallic Chemistry 689 (2004) 3641-3668), herein incorporated by reference in its entirety, describes many different catalysts for trimerization. These catalyst systems contain chromium, and with particular ligands, such as aromatic species (e.g. pyrrolyl) or multidentate heteratomic species. The chromium catalysts are typically activated by alkylaluminum and/or alkylaluminoxane activators. The article also describes group 4 and 5 early transition metals, such as Zr, V, Ta and Ti, and group 8 late transition metals, such as Ni, for showing some activity in trimerization.

Phillips has developed and patented chromium-based catalysts that are selective towards making 1-hexene from ethylene. The major byproduct appears to be 1-decene. SRI Consulting PEP Review 95-1-8 entitled "1-Hexene From Ethylene By the Phillips Trimerization Technology," available on-line at http://www.sriconsulting.com/PEP/Reports/Phase_95/RW95-1-8/RW95-1-8.html, herein incorporated by reference in its entirety, describes the Phillips standalone process for making 1-hexene based on Phillips trimerization technology. In this process, ethylene and a homogeneous catalyst in a solvent are fed to a reactor. The reactor is a stirred tank with heat removal coils. This reactor operates at 115 deg. C. and 49 kg/cm2 (~700 psia), and converts about 75% of the ethylene fed. This reactor is 42,300 gal (5655 ft3). A spare reactor is provided, since waxy buildup on the cooling coils may necessitate lengthy shutdowns for cleaning. The feed is approximately 29,000 lb/hr cyclohexane solvent (with catalyst) plus 36,000 lb/hr ethylene (27,000 fresh feed and 9,000 recycle). It is estimated that the resident time in the reactor is on average 4 to 5 hours. Selectivity in the Phillips process by weight is about 93% to 1-hexene, 1% to other C6s, 1% to octenes, and 5% to decenes. The effluent from the reactor is contacted with octanol to kill the catalyst from further reaction. The effluent then goes to an ethylene column, where unconverted ethylene is taken overhead and recycled to the reactor. Because ethylene is so volatile, an expensive cryogenic column must be used. Four more distillation columns follow to remove hexene, cyclohexane solvent, octene, and decene. Some of these are run under vacuum, which again makes for expensive hardware and operations. The bottoms from the decene tower is a small stream containing mainly octanol and deactivated catalyst. This stream is treated with caustic and then with acid to remove the catalyst by precipitation and by solution in an aqueous phase, which is separated from the organic phase containing the octanol. Octanol may then be recycled.

U.S. Pat. No. 5,382,738 to Reagen et al., herein incorporated by reference in its entirety, discloses catalyst systems comprising inorganic oxides, modified with a metal alkyl and an unsaturated hydrocarbon, which can be used to support a metal source, such as, for example, chromium, and a pyrrole-containing compound. The resultant catalyst systems can be used to oligomerize and/or trimerize olefins.

U.S. Pat. No. 5,451,645 to Reagen et al., herein incorporated by reference in its entirety, discloses novel chromium-containing compounds prepared by forming a mixture of a chromium salt, a metal amide, and an ether. These novel chromium-containing, or chromium pyrrolide compounds, with a metal alkyl and an unsaturated hydrocarbon, can be used as a cocatalyst system in the presence of an olefin polymerization catalyst system to produce a comonomer in-situ.

U.S. Pat. No. 5,523,507 to Regen et al., herein incorporated by reference in its entirety, discloses novel chromium-containing compounds prepared by forming a mixture of the chromium salt, a metal amide, and an ether either supported or unsupported. These novel chromium-containing compounds are activated by non-hydrolyzed alkyl aluminum compound and a Lewis acid.

U.S. Pat. No. 5,543,375 to Lashier et al., herein incorporated by reference in its entirety, discloses a process to stabilize and/or reactivate an olefin production catalyst system which comprises contacting an olefin production catalyst system, either before or after use, with an aromatic compound, but prior to contacting the system with a reactant.

U.S. Pat. No. 5,563,312 to Knudsen et al., herein incorporated by reference in its entirety, discloses a process to stabilize and/or reactivate an olefin production catalyst system which comprises contacting an olefin production catalyst system, either before or after use, with an aromatic compound.

U.S. Pat. No. 5,859,303 to Lashier, herein incorporated by reference in its entirety, discloses a process in which the solvent is the product of the olefin oligomerization process. This novel process uses a catalyst essentially comprising a chromium compound or chromium salt, a pyrrole-containing compound, and an alkyl compound.

European Pat. No. 0 668 106 to Freeman et al., herein incorporated by reference in its entirety, discloses a process which will effectively deactivate, inhibit, and/or "kill" an olefin production catalyst, and halt polymer production in an olefin production process. It further provides for a process which can remove an olefin production catalyst from the product stream, and recover catalyst by-products for recycle, and/or recovery.

PCT publication WO 99/19280A1 to Woodard et al., herein incorporated by reference in its entirety, discloses a process in which olefins are trimerized in the presence of a catalyst system comprising a chromium source, a pyrrole containing compound and a metal alkyl. The process is preformed in a reactor and provides for a separator for collection of the desired products.

PCT publications WO 2004/056478 to Blann et al. and WO 2004/056479 to Blann et al., both hereby incorporated by reference in their entirety, disclose processes and catalysts to prepare an olefinic stream with more than 30% of 1-octene. The catalysts for this system are those that contain chromium or a chromium salt and a heteroatomic ligand A need exists for an improved process to generate comonomer in a pre-reactor immediately before the polymerization reactor without isolation of the comonomer. More particularly, a need exists for a reaction/separation process to generate 1-hexene from ethylene immediately before the LLDPE polymerization reactor with no isolation or storage of the hexene produced.

SUMMARY OF THE INVENTION

It has been discovered that it is possible to generate 1-hexene and other comonomers from ethylene immediately before the polyethylene polymerization reactor with no isolation or storage of the hexene or other comonomer produced.

According to the present disclosure, an advantageous method for generating 1-hexene and other comonomers immediately before a polyethylene polymerization reactor, includes the steps of: providing an in-line comonomer synthesis reactor and a downstream gas/liquid phase separator prior to a polyethylene polymerization reactor; feeding ethylene monomer and a catalyst in a solvent to the comonomer synthesis reactor; reacting the ethylene monomer and the catalyst in solvent under reaction conditions to produce an effluent stream comprising ethylene monomer and comonomer selected from the group consisting of 1-hexene, 1-octene; 1-decene and mixtures thereof; passing the effluent stream from the comonomer synthesis reactor to the downstream gas/liquid phase separator to separate a gas stream from a bottoms stream, wherein the gas stream is a mixture of ethylene monomer, and the comonomer; purging from the bottom stream spent catalyst and purge heavies, and recycling the catalyst in solvent to the comonomer synthesis reactor; and passing the gas stream to the polyethylene polymerization reactor to provide a comonomer source.

A further aspect of the present disclosure relates to an advantageous method for generating 1-hexene and other comonomers immediately before a polyethylene polymerization reactor, which includes the steps of: providing an in-line comonomer synthesis reactor prior to a polyethylene polymerization reactor, wherein the reactor is a fixed bed type with a catalyst in a fixed position; feeding ethylene monomer to the comonomer synthesis reactor; reacting the ethylene monomer and the catalyst under reaction conditions to produce an effluent stream comprising ethylene monomer and comonomer selected from the group consisting of 1-hexene, 1-octene; 1-decene and mixtures thereof; and directing the effluent stream to the polyethylene polymerization reactor to provide a comonomer source.

Another aspect of the present disclosure relates to an advantageous method for generating 1-hexene and other comonomers immediately before a polyethylene polymerization reactor, which includes the steps of: providing an in-line comonomer synthesis reactor and a downstream gas/liquid phase separator prior to a polyethylene polymerization reactor; feeding ethylene monomer and a catalyst in a solvent to the comonomer synthesis reactor; reacting the ethylene monomer and the catalyst in solvent under reaction conditions to produce an effluent stream comprising ethylene monomer and comonomer selected from the group consisting of 1-hexene, 1-octene; 1-decene and mixtures thereof; passing the effluent stream from the comonomer synthesis reactor to the downstream gas/liquid phase separator to separate a gas stream from a bottom stream, wherein the gas stream is a mixture of ethylene monomer, and the comonomer; and transporting without isolation or storage the gas stream to the polyethylene polymerization reactor to provide a comonomer source.

Numerous advantages result from the advantageous method of preparing comonomer from monomer immediately before the polymerization reactor disclosed herein and the uses/applications therefore.

For example, in exemplary embodiments of the present disclosure, the disclosed method for preparing comonomer from monomer immediately before the polymerization reactor provides for substantial capital and operational cost savings over a conventional standalone process for manufacturing comonomer.

In a further exemplary embodiment of the present disclosure, the disclosed method for preparing comonomer from monomer immediately before the polymerization reactor eliminates the need to store or isolate the monomer produced.

In a further exemplary embodiment of the present disclosure, the disclosed method for preparing comonomer from monomer immediately before the polymerization reactor provides for range of catalysts for the oligomerization reaction.

In a further exemplary embodiment of the present disclosure, the disclosed method for preparing comonomer from monomer immediately before the polymerization reactor provides for the capability to produce both hexene and octene through catalyst selection.

In a further exemplary embodiment of the present disclosure, the disclosed method for preparing comonomer from monomer immediately before the polymerization reactor provides for process simplification, and the associated benefits of such.

In a further exemplary embodiment of the present disclosure, the disclosed method for preparing comonomer from monomer immediately before the polymerization reactor provides for continual removal of hexene from the comonomer synthesis reactor zone, which reduces the formation of decene byproduct.

These and other advantages, features and attributes of the disclosed method for preparing comonomer from monomer immediately before the polymerization reactor of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein.

DETAILED DESCRIPTION OF THE INVENTION

The present invention relates to an improved reaction and separation process for generating comonomer (e.g. 1-hexene)

from monomer (e.g. ethylene). In one exemplary embodiment of the present invention, the improved process may be implemented immediately before the polymerization reactor with no isolation or storage of the hexene produced. Hexene is swept out of the reaction zone or loop along with unconverted ethylene, leaving behind catalyst and heavy solvent. Specific hardware implementations of this concept include a "bubbling pot" and a reactor/knockout pot pumparound.

In an alternative embodiment of the present invention, 1-octene is produced from ethylene through proper selection of the catalyst for the oligomerization reaction. The improved process of the instant invention is also adaptable to catalysts which produce both hexene and octene.

Figure 1:
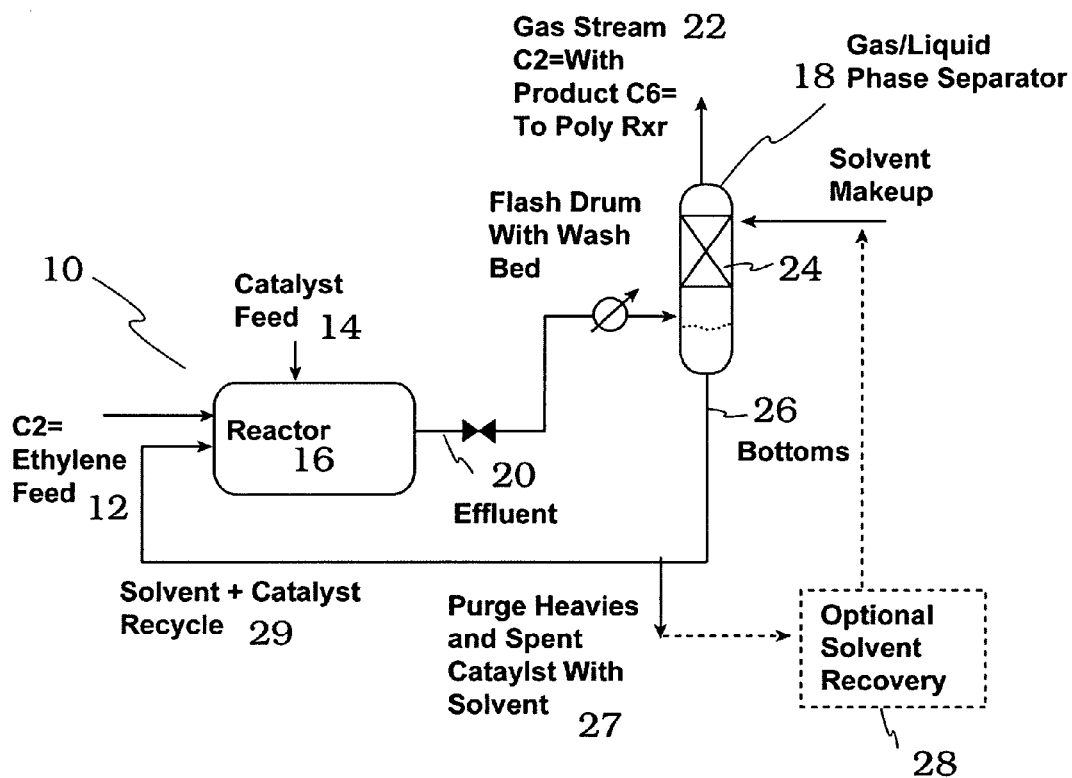
FIG. 1 depicts an illustrative schematic of the in-line process for comonomer generation utilizing a comonomer synthesis reactor and a downstream gas/liquid phase separator.

FIG. 1 depicts one exemplary process schematic of the improved in-line reaction and separation process 10 of the instant invention. In this configuration, ethylene feed 12 and catalyst feed 14 are fed to a comonomer synthesis reactor 16 (also referred to as an oligomerization reactor). The comonomer synthesis reactor 16 may be of various types, including, but not limited to a stirred tank reactor, more than one agitated vessel in series, and a long, thin tube-like contactor. If the catalyst is in the form of a fixed bed rather than slurry or solution, it may be contained in a contactor type of reactor.

Catalysts suitable for the present invention are those that comprise a reactive transition metal source catalytically able to selectively trimerize or tetramerize olefins. Exemplary metal sources include, but are not limited to, chromium, vanadium, tantalum, and titanium. Exemplary catalyst types include, but are not limited to, chromium, vanadium, tantalum and titanium trimerization and/or tetramerization catalysts. Preferably the catalytic system comprises a titanium source, more preferably a tantalum source and even more preferably a chromium source for improved catalyst activity and selectivity.

If a chromium source is used, one or more organic ligands may also be present in addition to any inorganic ligands, wherein the oxidation state of the chromium is from 0 to 6. Exemplary organic ligands are organic radicals having from 1 to 20 carbon atoms per radical, which are selected from the group consisting of alkyl, alkoxy, ether, ester, ketone, phosphine and/or amine. The organic ligands may also include heteroatoms. The organic radicals may be straight chained or branched, cyclic or acyclic, aromatic or aliphatic and any combination may be present in the metal complex. The organic radical may include multiple heteroatoms that are linked by bridging groups to provide for multidentate complexation with the chromium source.

Preferred organic radicals include "pyrrole-containing" compounds. For the purposes of this invention "pyrrole-containing" compounds refers to those that include a pyrrole molecular fragment or a derivative of hydrogen pyrrolide, i.e. pyrrole ($C_4H_5N$). Non-limiting examples of "pyrrole-containing" compounds include 2,3-dimethylpyrrole, 2,5-dimethylpyrrole, 2,4-dimethyl-3-ethylpyrrole, 2-acetylpyrrole, 3-acetyl-2,5-dimethylpyrrole and ethyl-3,5-dimethyl-2-pyrrolecarboxylate.

Bridging organic radicals of the present invention include those with one or more phosphorous heteroatoms such as PNP ligands. Non-limiting examples include (2-methyloxyphenyl)$_2$PN(methyl)P(2-methyoxyphenyl)$_2$, (3-methyloxyphenyl)$_2$PN(methyl)P(3-methyoxyphenyl)$_2$, (4-methyloxyphenyl)$_2$PN-(methyl)P(4-methyoxyphenyl)$_2$, (2-methyloxyphenyl)$_2$PN(ethyl)P(2-methyoxyphenyl)$_2$, (2-methyloxyphenyl)$_2$PN(isopropyl)P(2-methyoxyphenyl)$_2$, (2-methyloxyphenyl)$_2$PN(methyl)P(3-methyoxyphenyl)$_2$, (2-methyloxyphenyl)$_2$PN-(methyl)P(4-methyoxyphenyl)$_2$, (4-fluorophenyl)$_2$PN(methyl)P(4-fluorophenyl)$_2$, and (2-fluorophenyl)$_2$PN(benzyl)P(2-fluorophenyl)$_2$.

Bridging organic radicals of the present invention also include those with a hydrocarbon bridge between the phosphorous heteroatoms. Non-limiting examples include 1-(2-methyoxyphenyl)(phenyl)phosphino-2-(2-methyoxyphenyl)(phenyl)phosphinoethane, 1-di(3-methyoxyphenyl)phosphino-2-(2-methyoxyphenyl)(phenyl)phosphinoethane, 1-(2-methyoxyphenyl)-(phenyl)phosphino-3-(2-methyoxyphenyl)(phenyl)phosphinopropane, 1-(4-methyoxyphenyl)(phenyl)phosphino-2-(4-methyoxyphenyl)(phenyl)phosphino-propane, 1-(2-methyoxyphenyl)(phenyl)phosphino-2-(2-methyoxyphenyl)-(phenyl)phosphinopropane, and 1-diphenylphosphino-2-(2-fluoro-phenyl)(phenyl)phosphinoethane.

The catalyst system may also include an activator. The activator may be any compound that generates an active catalyst when combined with the transition metal compound and the organic and/or inorganic ligand. Exemplary compounds for activators include, but are not limited to, organoaluminum compounds, organoboron compounds, organic metal salts, and inorganic acids and salts. Preferred activators include alkylaluminum compounds, such as triethylaluminum, trimethylaluminum, triisobutylaluminum and alkylaluminoxanes. Preferred alkylaluminoxanes include methylaluminoxane, ethylaluminoxane and modified alkylaluminoxanes, such as modified methylaluminoxane (MMAO). Ratios of the aluminum activator to the transition metal may be from 1:1 to 10,000:1, preferably from about 1:1 to 5000:1, more preferably from about 1:1 to 1000:1 and even more preferably from about 1:1 to 500:1.

The comonomer synthesis reactor 16 is separate from the subsequent gas/liquid phase separator 18, which allows for separate control of reaction and separation conditions. The reactor temperature and pressure are controlled to provide for acceptable reaction rates and selectivities, as well as to provide for phase separation.

With regard to catalyst solvent, there is flexibility as far as what catalyst solvent, if any, may be used. If a catalyst solvent is used, it should be less volatile than hexene, and preferably less volatile than octene, such that it is not swept out along with hexene product. If decene recovery is desired and the solvent is a hydrocarbon, then the solvent should have volatility different than decene. On the other hand, if a solvent is used that is compatible with the polymerization process (e.g. isobutane), it may be acceptable to allow large amounts of that solvent to leave the oligomerization reactor 16 along with the ethylene and hexene. Examples of other suitable catalyst solvents include C5+ paraffins (preferable branched, e.g. isopentane), cycloparaffins, and aromatics. If the catalyst is in the form of a fixed bed or a slurry, it may not require additional extraneous solvent.

Reaction conditions are selected to give from about 5% to about 75%, preferably from about 10% to about 50% conversion of feed ethylene. Some of the chromium catalysts disclosed by Phillips, for example as disclosed in U.S. Pat. No. 5,543,375, permit a range of conditions. One exemplary, but non-limiting set of conditions, is a reaction temperature of from about 80 to about 150° C., and a reaction pressure of from about 300 to about 700 psi. However, when utilizing an ethylene feed 12, a reaction temperature of from about 60 to about 110° C. is preferred. Process conditions may be tuned to obtain desired phase separations as well as reactivity. Residence time is flexible, and is chosen to provide a desired level of ethylene conversion. A range of average reaction residence time of from about 30 minutes to about 4 hours is contemplated when using Phillips catalysts with a backmixed or pump around type of comonomer synthesis reactor 16 where most of the catalyst in the reactor 16 at a given time is not "fresh", but has been circulating around for some time before becoming deactivated. The range of reaction residence times may depend on other factors, such as the nature and amount of the catalyst.

The effluent 20 from the comonomer synthesis reactor 16 is directed to the gas/liquid phase separator 18, where the gas stream 22 exits the separator 18. A catalyst deactivator (e.g. water or alcohol) may be added to effluent 20. The gas stream 22 contains predominately ethylene along with comonomer, such as 1-hexene or 1-octene. The gas/liquid phase separator 18 may include, but is not limited to, a simple knockout vessel or other one-stage phase separator, but it may also include some trays or packing 24 in the zone where vapor is going up, with reflux liquid flowing down, to sharpen the C6/C8 or C8/C10 separation and also to wash down any catalyst or heavies that were carried upwards. In one embodiment, the ethylene is bubbled through a stirred tank or pot, and exits into a vapor space above the liquid.

In another alternative embodiment, some ethylene (not shown) is added to the separator 18 below the feed entrance point, to strip out hexene or other comonomer (not shown) from the down-flowing solvent (not shown). The bottoms 26 from the separator 18, containing the catalyst, decene, and heavy solvent (if any), is predominately pumped back to the reactor 16. Heat exchangers (not shown) are in-line with the pump around flow. Where waxy buildup is an issue, spare heat exchangers may also be provided. For both the bubbling pot and the pumparound type reactor/separator configurations described above, a small portion of the bottoms stream 26, containing purge heavies, spent catalyst with heavy solvent (if any) 27, and decene is directed to an optional catalyst disposal and solvent recovery process 28. To minimize the load on solvent recovery process 28, it is desirable to have a catalyst with high productivity (grams of olefin converted divided by grams of catalyst used).

In the gas stream 22 from the gas/liquid phase separator 18, ethylene (also referred to as C2) is not recovered in high purity. This saves cryogenic ethylene column costs. Unconverted ethylene may be recycled back to the comonomer synthesis reactor 18, or sent on to another process (not shown), for example the downstream polyethylene polymerization process. Solvent and catalyst recycle 29 from the bottoms 26 of the gas/liquid phase separator 18 are sent back to the oligomerization reactor 16. Most octene products are swept out of the reactor or reactor/separator loop along with unconverted ethylene in the gas stream 22. The improved in-line reaction and separation process 10 does not include hexene/octene (also referred to as C6/C8) separation because some of the trace octene byproduct is used in the polymerization along with the hexene. Some trace octene may also exit the gas/liquid phase separator 18 in the bottoms stream 26 along with the decene (also referred to as C10) byproduct.

The improved reaction and separation process of the instant invention for generating monomer in a pre-reactor immediately before the polymerization reactor without isolation of the comonomer greatly simplifies the required process. The exemplary process schematic of FIG. 1 permits the number of separation towers to be reduced versus the standalone concept of producing comonomer. This results in significant operating and capital cost savings over conventional standalone processes for manufacturing comonomers, such as hexene. An additional benefit of the instant invention is that the continual removal of hexene from the comonomer synthesis reactor zone reduces the formation of decene byproduct. The improved reaction and separation process of the instant invention is compatible with a Phillips-type trimerization catalyst, but may also be useful with other homogeneous or heterogeneous selective oligomerization catalysts.

Figure 2:
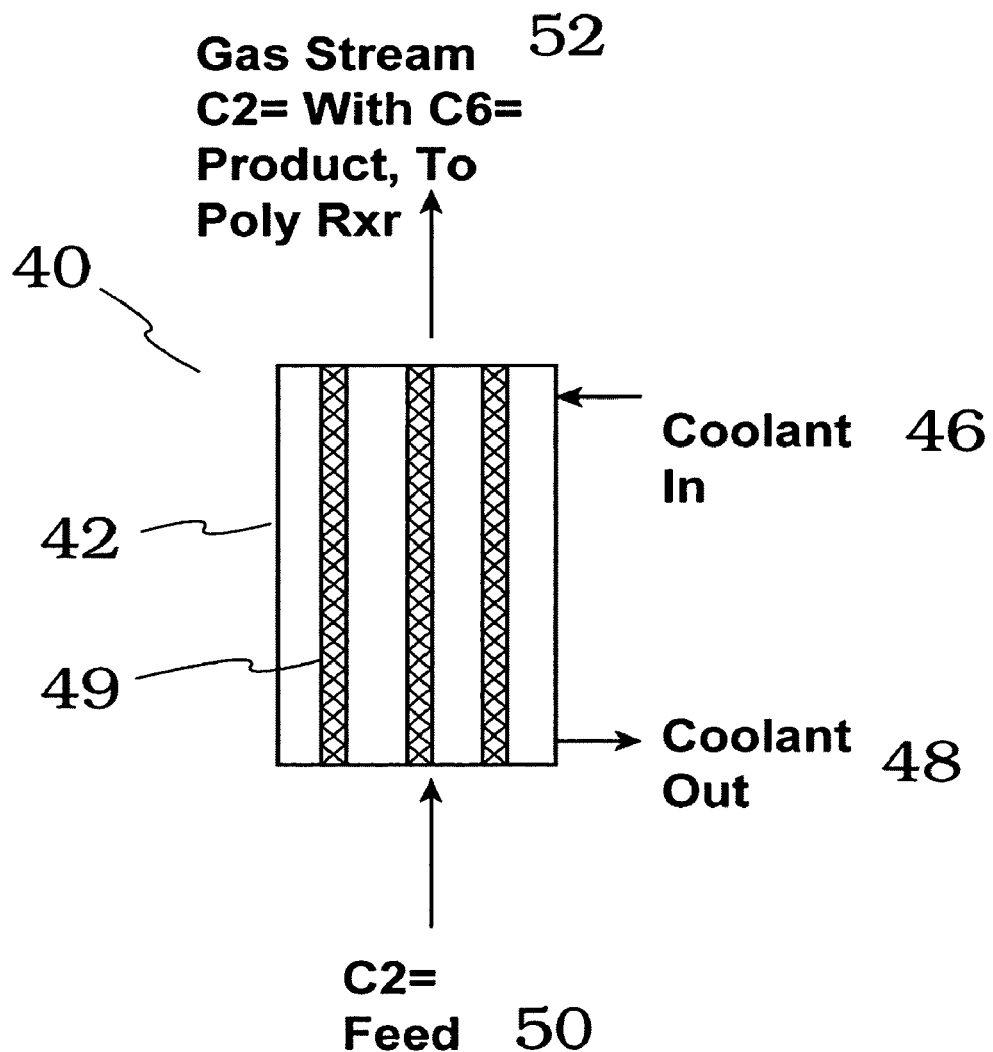
FIG. 2 depicts an illustrative schematic of the fixed bed reactors for in-line comonomer generation without a downstream gas/liquid phase separator in which catalyst is in the tubes with coolant.
Figure 3:
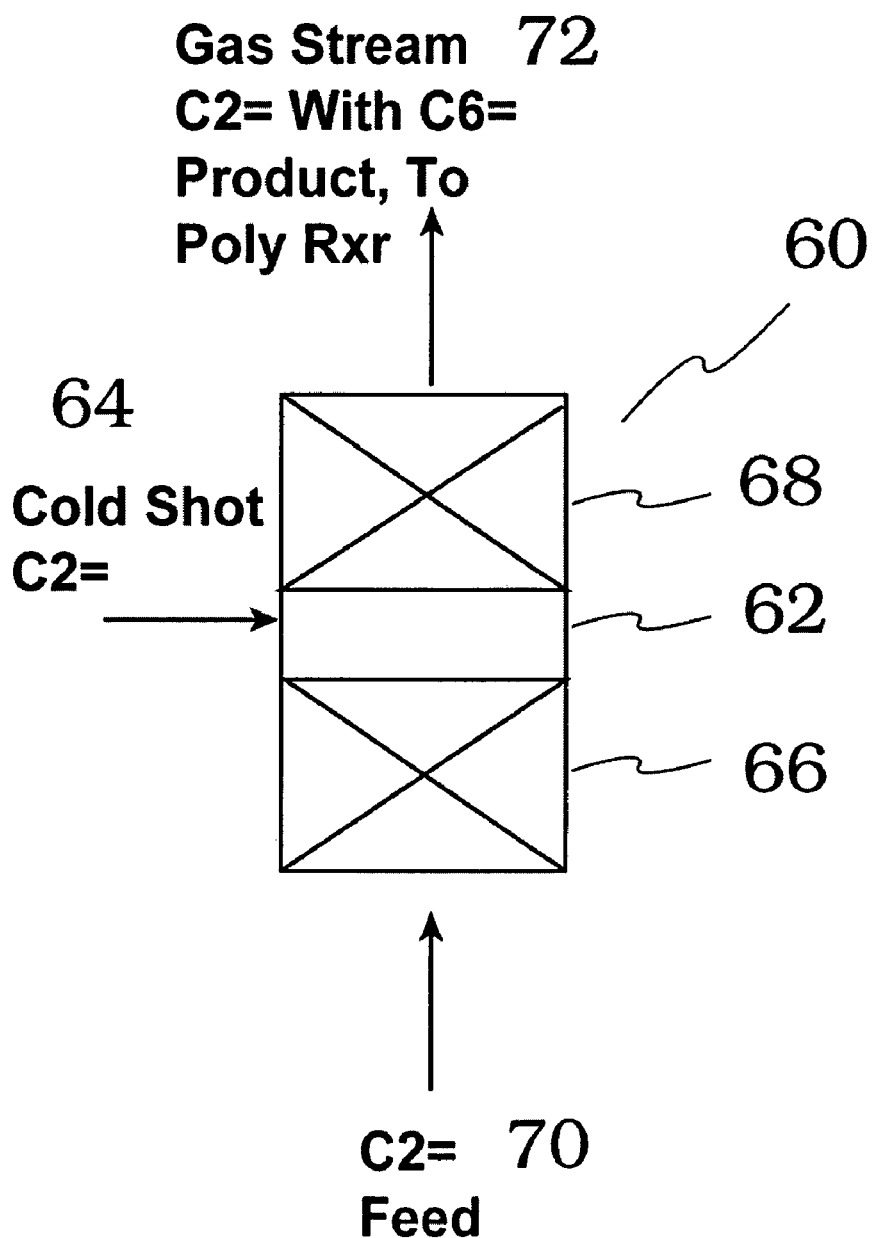
FIG. 3 depicts an illustrative schematic of the fixed bed reactors for in-line comonomer generation without a downstream gas/liquid phase separator in which cold shot cooling is utilized.

FIGS. 2 and 3 depict two other exemplary process schematics of improved in-line comonomer generation processes 40, 60 of the instant invention that do not include a gas/liquid phase separator. These embodiments represent an even more simplified approach. In both FIGS. 2 and 3, fixed bed reactor types are used where the catalyst is in a fixed position, and ethylene is fed past it. Catalyst types may include, but are not limited to, chromium, vanadium, tantalum and titanium trimerization and/or tetramerization catalysts.

As comonomer (e.g. hexene) is produced, it is swept into the gas phase and carried out of the reactor. The precise form of the catalyst may include, but is not limited to, a solid, including active catalytic species anchored to a support, or in the form of a porous solid bed or monolith, which is wetted with soluble catalyst in a heavy solvent. The solvent with catalyst may be trickled through the bed, to renew the solvent over time.

In gas/solids systems, temperature control can be an issue. Using 47 kcal/mol hexene for heat of reaction, it can be estimated that for undiluted ethylene, a 10% conversion to hexene would generate about a 110 deg. C. temperature rise if there were no heat removal from the reactor. Also depicted in FIGS. 2 and 3 are two exemplary embodiments for managing the reaction heat generated.

In FIG. 2, the heat exchange capability is put into the reaction zone, for example, by loading the catalyst in 1"-6" diameter tubes surrounded by a cooling medium. FIG. 2 depicts a comonomer synthesis reactor 42 with catalyst in tubes 44 with coolant. Coolant enters and exits the comonomer synthesis reactor 42 through the coolant in 46 and coolant out 48 ports respectively. Ethylene (C2 feed) 50 enters the comonomer synthesis reactor 42 and reacts to form a gas stream 52 containing predominately ethylene (C2) along with comonomer, such as 1-hexene or 1-octene, which may be transferred directly to a downstream polyethylene polymerization reactor.

In FIG. 3, the reactor is divided into two or more catalyst beds, and cool feed or diluent is injected before each stage. FIG. 3 depicts a comonomer synthesis reactor 62 with cold shot cooling of C2 64 between the first reaction stage 66 and the second reaction stage 68 of the comonomer synthesis reactor 62. Ethylene (C2) feed 70 enters the comonomer synthesis reactor 62 and again reacts to form a gas stream 72 containing predominately ethylene (C2) along with comonomer, such as 1-hexene or 1-octene, which may be transferred directly to a downstream polyethylene polymerization reactor (not shown).

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

What is claimed is:

1. An in-line method for generating comonomer for input to a polyethylene polymerization reactor comprising the following steps:

providing an in-line comonomer synthesis reactor and a downstream gas/liquid phase separator prior to a polyethylene polymerization reactor;

feeding ethylene monomer and a catalyst in a solvent to said comonomer synthesis reactor;

reacting said ethylene monomer and said catalyst in solvent under reaction conditions to produce an effluent stream comprising ethylene monomer and comonomer selected from the group consisting of 1-hexene, 1-octene, 1-decene, and mixtures thereof;

passing said effluent stream from said comonomer synthesis reactor to said downstream gas/liquid phase separator to separate a gas stream from a bottoms stream, wherein said gas stream is a mixture of ethylene monomer, and said comonomer;

adding ethylene to said gas/liquid phase separator below the feed entrance point of said effluent stream to separate said comonomer from said solvent;

purging from said bottoms stream spent catalyst and purge heavies, and recycling said catalyst in solvent to said comonomer synthesis reactor; and passing said gas stream to said polyethylene polymerization reactor to provide a comonomer source.

2. The in-line method of claim 1, wherein said gas stream is not stored or isolated prior to entering said polyethylene polymerization reactor.

3. The in-line method of claim 1, wherein said comonomer synthesis reactor is a stirred tank reactor, more than one agitated vessel in series, or a tube-like contactor.

4. The in-line method of claim 1, wherein said catalyst is selected from the group consisting of a chromium trimerization catalyst, a vanadium trimerization catalyst, a tantalum trimerization catalyst, a titanium trimerization catalyst, a chromium tetramerization catalyst, a vanadium tetramerization catalyst, a tantalum tetramerization catalyst, and a titanium tetramerization catalyst.

5. The in-line method of claim 1, wherein said catalyst further comprises one or more organic ligands, one or more inorganic ligands, one or more activators, or mixtures thereof.

6. The in-line method of claim 1, wherein said solvent has a volatility less than 1-hexene and 1-octene.

7. The in-line method of claim 6, wherein said solvent is selected from the group consisting of isobutane, isopentane, cycloparaffins, and aromatics.

8. The in-line method of claim 1, wherein said reaction conditions yield from about 5% to about 75% conversion of said ethylene monomer.

9. The in-line method of claim 8, wherein said reaction conditions yield from about 10% to about 50% conversion of said ethylene monomer.

10. The in-line method of claim 8, wherein said reaction conditions comprise a reaction temperature from about 80 to about 150° C., a reaction pressure from about 300 to about 700 psi, and a reaction residence time from about 30 minutes to about 4 hours.

11. The in-line method of claim 1, wherein a catalyst deactivator is added to said effluent stream exiting from said comonomer synthesis reactor.

12. The in-line method of claim 11, wherein said catalyst deactivator is water or alcohol.

13. The in-line method of claim 1, wherein said gas/liquid phase separator comprises a knockout vessel, a stirred tank or pot, or other one-stage phase separator.

14. The in-line method of claim 13, wherein said gas/liquid phase separator further comprises trays or packing in the vapor zone.

15. The in-line method of claim 1, wherein said gas stream comprises predominately ethylene along with 1-hexene and 1-octene.

16. The in-line method of claim 1, wherein said bottoms stream comprises ethylene monomer, spent catalyst, purge heavies, catalyst in solvent, 1-octene and 1-decene.

17. The in-line method of claim 1 further comprising the step of adding ethylene monomer to said gas/liquid phase separator to strip out comonomer from down-flowing solvent.

18. The in-line method of claim 1 further comprising the step of directing to a catalyst disposal and solvent recovery process said spent catalyst and said purge heavies.

19. An in-line method for generating comonomer for input to a polyethylene polymerization reactor comprising the following steps:

providing an in-line comonomer synthesis reactor and a downstream gas/liquid phase separator prior to a polyethylene polymerization reactor;

feeding ethylene monomer and a catalyst in a solvent to said comonomer synthesis reactor;

reacting said ethylene monomer and said catalyst in solvent under reaction conditions to produce an effluent stream comprising ethylene monomer and 1-hexene comonomer;

passing said effluent stream from said comonomer synthesis reactor to said downstream gas/liquid phase separator to separate a gas stream from a bottom stream, wherein said gas stream is a mixture of ethylene monomer, and said 1-hexane comonomer; adding ethylene to said gas/liquid phase separator below the feed entrance point of said effluent stream to separate said 1-hexene comonomer from said solvent; and transporting without isolation or storage said gas stream to said polyethylene polymerization reactor to provide a comonomer source wherein said solvent is less volatile than said 1-hexene comonomer.

20. The in-line method of claim 19, wherein said catalyst is selected from the group consisting of a chromium trimerization catalyst, a vanadium trimerization catalyst, a tantalum trimerization catalyst, a titanium trimerization catalyst, a chromium tetramerization catalyst, a vanadium tetramerization catalyst, a tantalum tetramerization catalyst, and a titanium tetramerization catalyst.

* * * * *